United States Patent [19]

Milovidov

[11] Patent Number: 4,533,258

[45] Date of Patent: Aug. 6, 1985

[54] METHOD OF DETERMINING THE CONTENT OF COMBUSTIBLES IN THE END PRODUCTS OF FUEL COMBUSTION AND APPARATUS REALIZING SAID METHOD

[76] Inventor: Boris A. Milovidov, ulitsa Kalinina, 143, kv. 25, Pavlodar, U.S.S.R.

[21] Appl. No.: 626,585

[22] Filed: Jul. 2, 1984

Related U.S. Application Data

[63] Continuation of Ser. No. 395,465, Jul. 6, 1982, abandoned.

[51] Int. Cl.³ ............................................. G01N 25/22
[52] U.S. Cl. ........................................ 374/36; 374/37; 374/38
[58] Field of Search ....................... 374/33, 36, 37, 38; 422/51, 98; 436/147, 149

[56] References Cited

U.S. PATENT DOCUMENTS

| | | | |
|---|---|---|---|
| 4,059,007 | 11/1977 | Miller et al. | 374/36 |
| 4,088,447 | 5/1978 | Walker | 422/51 |
| 4,305,724 | 12/1981 | Micko | 422/88 |
| 4,329,873 | 5/1982 | Maeda | 422/51 |
| 4,329,874 | 5/1982 | Maeda | 374/36 |

*Primary Examiner*—Charles Frankfort
*Assistant Examiner*—David R. Schuster
*Attorney, Agent, or Firm*—Burgess, Ryan and Wayne

[57] ABSTRACT

The apparatus materializing the method of determining the content of combustibles in the products of fuel combustion incorporates an oven with an electric heater connected into the load circuit of a controllable voltage source. The oven is provided with a pipe for introducing a sample of the end products of fuel combustion and with pipes for admitting an oxidizing agent and removing the end products of combustion of the combustibles. The sample is heated in the presence of the oxidizing agent to a temperature equal to or higher than the fire point of the combustibles present in the sample which, consequently, burn down. The temperature during the process of combustion is maintained constant with the aid of a temperature controller having its input connected to a temperature transducer located in the oven and its output connected to the output of the controllable voltage source. A meter of electric power connected into the external circuit of the voltage source serves to measure the power consumed by the electric heater in maintaining the constant temperature, the content of combustibles being judged by said measurements.

4 Claims, 3 Drawing Figures

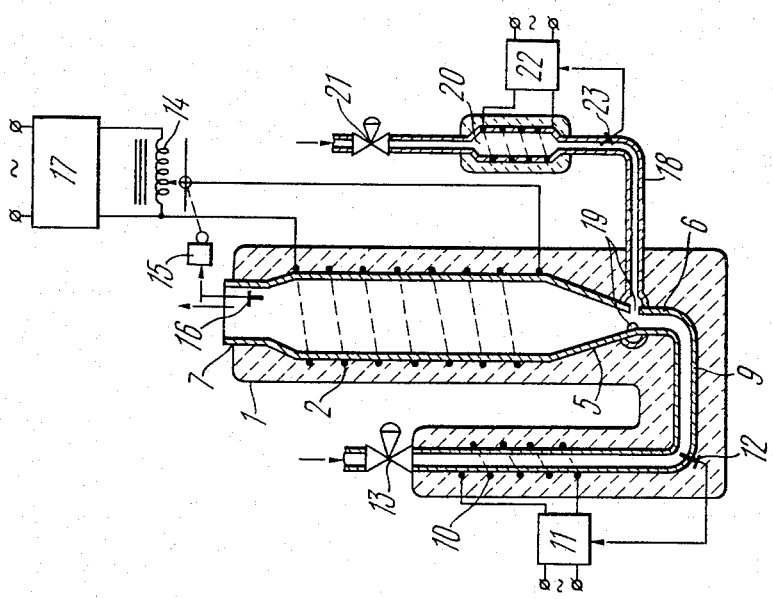
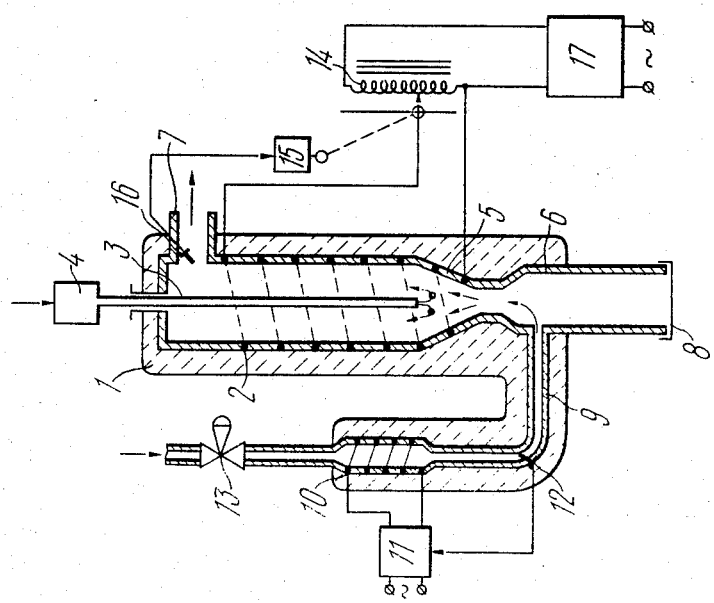

METHOD OF DETERMINING THE CONTENT OF COMBUSTIBLES IN THE END PRODUCTS OF FUEL COMBUSTION AND APPARATUS REALIZING SAID METHOD

This is a continuation, of application Ser. No. 395,465 filed July 6, 1982, now abandoned.

FIELD OF THE INVENTION

The invention relates to heat power engineering, being concerned with the monitoring and controlling fuel combustion, and has special reference to a method of determining the content of combustibles in the end products of fuel combustion and an apparatus realizing said method.

The invention is intended for use in systems monitoring the combustion of fuel, pulverized coal before all, so as to ensure its complete combustion in boiler plant and industrial furnaces. Automatic combustion control and express analysis of a fuel in use and the combustion residues obtained are other fields of application.

BACKGROUND OF THE INVENTION

Incompleteness of combustion processes is betrayed by the presence of combustibles in the products of combustion, i.e. of combustible gases determining the amount of chemical incomplete combustion of fuel and of solid particles of fuel indicating the amount of unburned carbon.

The two factors mentioned are attributed to feeding the fuel and oxidizing agent at a ratio other than the specified one, deviating from a specified procedure of preparing the fuel and oxidizing agent, poor uniformity of intermixing thereof, failure to observe a specified optimal temperature condition of combustion. An inadequate construction of the furnace used may also lead to incomplete combustion and unburned carbon. A remedy enabling these drawbacks to be eliminated partially of fully is either an effective control of combustion or a reconstruction of the furnace.

The presence of said drawbacks can be established by monitoring—with a requisite accuracy and in good time—the degree of incomplete burning as defined by the content of combustibles in the end products of fuel combustion.

The determination of the unburned carbon, which is the source of fuel loss with the slag and effluent gas, invites significant difficulties. Varying with the operating conditions such as the milling fineness of fuel particles, the way the fuel is being mixed with the oxidizing agent, the temperature of the process, etc., the unburned carbon is quantitatively defined by the carbon content of the ash residue where carbon is present in the form of reluctantly-burning coke particles.

At present, the content of combustibles in the ash residue is determined mainly at the laboratory from the loss in the weight of an ash sample after reburning same in a muffle furnace. Recurrent monitoring on these lines, the result of which remains unknown for several hours after a sample has been taken, fails to provide for an effective combustion control in good time. As a result, unburned fuel can be carried away with the products of combustion during an interval of time sufficiently long to cause excessive fuel consumption.

The problem of a more effective combustion control has been tackled so far to some extent only.

There is known a method of determining the content of combustibles in the end products of fuel combustion (cf., for example, USSR Inventor's Certificate No. 391,355, Cl. F 23 N 5/24) according to which a sample of end products of fuel combustion is introduced into the space between the plates of a capacitor. The resulting change in the capacitance defines the dielectric constant of the sample and the changes in the dielectric constant indicate the content of carbon in the end products of fuel consumption.

However, this method of determining the content of combustibles lacks accuracy, for various metal oxides present in the ash residue as well as moisture and other admixtures present in the sample distort the results of measurements.

Also known is an apparatus for determining the content of combustibles in the end products of fuel combustion (cf., for example, USSR Inventor's Certificate No. 375,449, Cl. F 23 N 5/24) incorporating a sampler, a sample separator setting apart the coarse fraction for the analysis, an electrically-driven screw feeder feeding the sample for the analysis, a capacitor connected into a measuring circuit and used to introduce the sample between its plates, and a meter.

The elimination of the small fraction from the sample in the known apparatus impairs the representativeness of the sample. Foreign matter present in the sample and variations in the concentration of the components of the ash residue also influence the accuracy of measurements.

Closer than anything else to the disclosed method in point of technical essence is a known method of determining the content of combustibles in the end product of fuel combustion consisting in taking a sample of the end products of fuel combustion, introducing the sample into a heating zone of an electric heater, heating the sample in the presence of an oxidizing agent to a temperature equal to or greater than the fire point of the combustibles contained therein which, consequently, inflame and finding the content of combustibles from the amount of heat liberated during the combustion, measurements of the temperature in the zone of heating—which varies directly with said amount of heat—being taken to that end (cf. an article "Ustroistva dlya opredeleniya poter's mekhanicheskim nedozhogom topliva" by Popov K. N., Agafonov E. V. and Matonin L. N., in Russian, in the monthly "Elektricheskie stantsii", No. I, 1973).

The known method also lacks accuracy, especially in the case of a continuous determination of the content of combustion in samples fed without interruption, for any change in the temperature influences the amount of heat lost into the surroundings and with the end products of combustion.

Further known is an apparatus for determining the content of combustibles in the end products of fuel combustion which realizes the known method referred to above. Said apparatus incorporates an oven with electric heaters, a pipe which is connected to a sampler and serves to introduce a sample of the end products of fuel combustion and pipes for feeding an oxidizing agent and removing the end products of combustion of the combustibles. The amount of heat liberated during the combustion of the combustibles is determined with the aid of temperature transducers (thermocouples) provided in the heating zone of the apparatus.

A changing temperature of the sample and structural members of the oven influences the amount of heat escaping into the surroundings with the end products of combustion. Some of the heat accumulates in the structural members of the oven in the heating zone. This all results in a disproportion between the heat liberated due to the combustion of the combustibles and the changes in the temperature. Apart from that, the temperature level used as reference in reading the changes in the temperature may shift, rendering the determination of the content of the combustibles more inaccurate. The known apparatus also lacks reliability, for any possible increase in the content of combustibles may cause a rise of the temperature in the heating zone to a point detrimental to the electric heater and leading to slagging of the oven.

SUMMARY OF THE INVENTION

It is an object of the invention to provide a method of determining the content of combustibles in the end products of fuel combustion and an apparatus realizing said method which ensure a higher than ever before accuracy in determining the content of combustibles.

Another object of the invention is to provide an apparatus for determining the content of combustibles in the end products of fuel combustion with an inherently high operational reliability.

Said objects are realized by the fact that in a method of determining the content of combustibles in the end products of fuel combustion consisting in taking a sample of the end products of fuel combustion, introducing the sample into a heating zone of an electric heater, heating the sample in the presence of an oxidizing agent to a temperature equal to or higher than the fire point of the combustibles which, consequently, burn down, the content of combustibles being judged by the heat thus liberated, in accordance with the invention, the temperature in the heating zone is maintained constant during the process of combustion of the combustibles and the power of the electric heater consumed in maintaining the constant temperature is being measured, said power varying directly with the amount of heat liberated due to the combustion of the combustibles.

Said objects are also realized by the fact that in an apparatus for determining the content of combustibles in the end products of fuel combustion incorporating an oven with an electric heater, a pipe which connects to a sampler and is used to introduce a sample of the end products of fuel combustion, pipes for feeding an oxidizing agent and removing the end products of combustion and a temperature transducer installed in the oven, there are provided in accordance with the invention a controllable voltage source in the load circuit whereof is connected the electric heater, a temperature controller having its input connected to the temperature transducer and its output to the controllable voltage source, and a meter of the electric power which is connected into the external circuit of the controllable voltage source.

To enable a temperature control to be effected in each particular area of the heating zone so as to keep the temperature in the zone as a whole at a constant level, improving thus the accuracy achieved in determining the content of combustibles, it is expedient that in the oven there are provided at least one additional electric heater located in the flow of the end products of combustion through the oven downstream of the main electric heater; additional controllable voltage sources, equalling in number with the additional electric heater, having their inputs connected to the input of the main controllable voltage source and having the respective additional electric heater connected into each of their load circuits; additional temperature transducers located in the oven, each in the heating zone of the respective additional electric heater; and additional temperature controllers having their inputs each connected to the respective additional temperature transducer and having their outputs each connected to the respective controllable voltage source, the meter of the electric power being connected into the common external circuit of the main controllable voltage source and the additional controllable voltage sources.

Providing for a constant temperature in the heating zone, the invention eliminates the slagging and overheating of the heaters, improving thus the reliability and extending the life of the apparatus. The invention also utilizes the heat liberated due to the combustion of the combustibles, saving thus the electric power required to determine the content thereof. By eliminating the effect of the heat flows resulting from temperature variations in the zone of heating, the invention enhances the accuracy of determining the content of combustibles. By measuring the electric power varying directly with the amount of heat liberated due to the combustion of the combustibles, the invention simplifies the transduction of the quantity to be determined into an electric signal, for the need in intermediate operations of transducing the amount of temperature changes into the amount of heat liberated is eliminated. Local temperature control from area to area in the zone of heating eliminates local factors influencing the pattern of heat flow, reducing thus the error in determining the content of combustibles.

BRIEF DESCRIPTION OF THE DRAWINGS

The invention will now be described by way of an example of a preferred embodiment thereof with reference to the accompanying drawings in which:

FIG. I is a schematic diagram of the apparatus for determining the content of combustibles in a sample of solid end products of fuel combustion in accordance with the invention, showing the oven, the pipe for introducing an oxidizing agent and the controllable electric heater located in the pipe in a sectional elevation;

FIG. 2 is a sectional elevation of the oven of the disclosed apparatus for determining the content of combustibles in a sample of the gaseous products of fuel combustion in accordance with the invention;

DETAILED DESCRIPTION OF THE INVENTION

Figure 3:
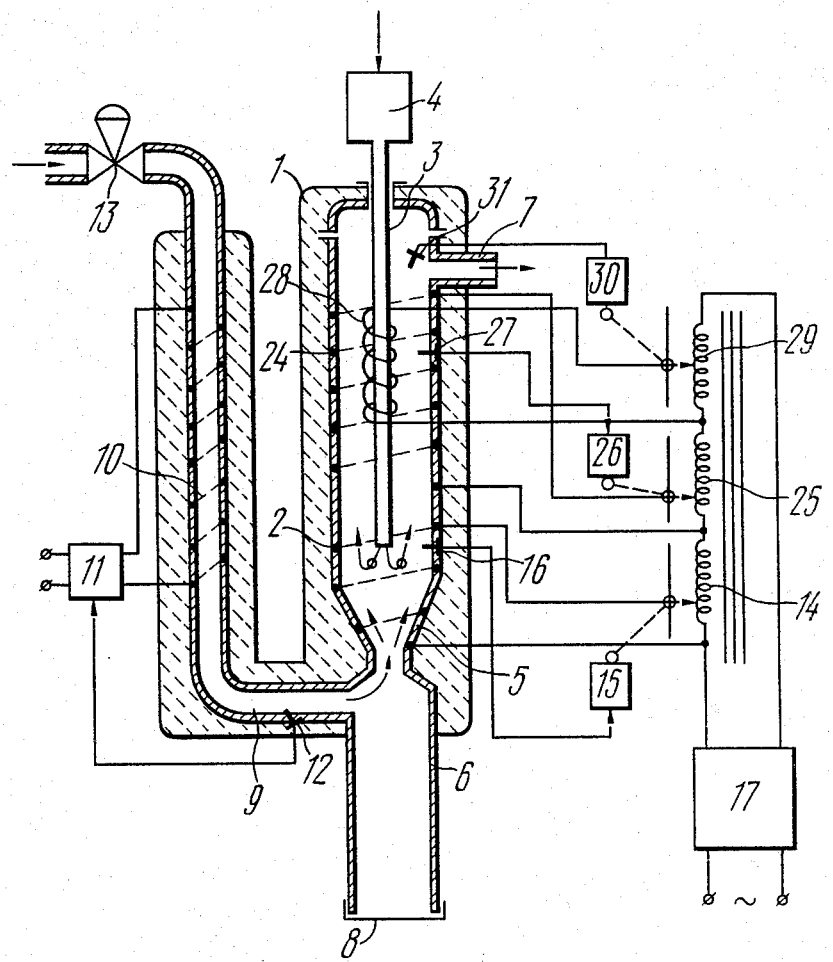
FIG. 3 is a view similar to FIG. I illustrating three areas of controlled heating in the zone of heating according to the invention.

The method of determining the content of combustibles in the end products of fuel combustion consists in that a sample of the end products of fuel combustion as taken, for example, from the flue of a boiler plant is introduced into the heating zone of the electric heater and heated there in the presence of an oxidizing agent to a temperature equal to or higher than the fire point of the combustibles present in the sample which, consequently, burn down. In the course of combustion of the combustibles, the temperature in the zone of heating is maintained at a constant level and the power of the electric heater used to keep the temperature constant is being measured, judging then the content of combustibles by these measurements.

The method is applicable in determining the content of combustibles in both solid and gaseous end products of combustion, i.e. is suitable to ascertain the unburned carbon and incomplete combustion, respectively. It may be employed in a batchwise monitoring of samples and in keeping a continuous check on the content of combustibles in a continuously fed sample.

For an implementation of the method of determining the content of combustibles in the solid end products of fuel combustion, e.g. the fly ash of a boiler plant, which are fed continuously, it is preferred to burn the solid combustible particles suspended in an ascending stream of a gaseous oxidizing agent. This promotes good contact between the particles and oxidizing agent, speeding up the process of combustion. The fact that the solid particles of the sample are fed in a counter-current flow with respect to the ascending stream of the oxidizing agent prolongs the period during which these particles are staying in the heating zone, contributing to its shrinking in both length and volume.

For a continuous determination of the content of combustibles in a sample of the gaseous end products of combustion, no vertical counter-current flow is required. It is preferred in this case to introduce the sample in a co-current flow with the oxidizing agent under the conditions of agitation after the temperature of the sample has been stabilized with the aid of a separate electric heater.

To eliminate an error resulting from variations in the ratio of the sample taken and the oxidizing agent and improve thus the accuracy of determining the content of combustibles, it is preferred to maintain their flow rates constant in either case with the aid of a flow governor of the oxidizing agent and a flow governor of the sample.

The apparatus realizing the method of determining the content of combustibles in a continuously fed sample of the solid end products of combustion, e.g. in the fly ash of a boiler plant, incorporates a vertically-arranged tube furnace I (FIG. I) with an electric heater 2 and a pipe 3 for feeding a sample of the end products of fuel combustion into the heating zone. The pipe 3 is connected to a smaller 4 and enters the oven I through the upper inlet thereof. Connected to the top of the oven I there is another pipe 7 serving to discharge the end products of combustion. A pipe 6 for introducing an oxidizing agent is connected to the lower inlet of the oven I by way of a divergent nozzle 5. To prevent the blocking up of the nozzle 5 at its inlet with coarse particles failing to be suspended in the counter-current stream of the oxidizing agent, the pipe 6 is provided in the form of a T-piece the lower part whereof is provided with a sealing arrangement 8 (e.g. a hydraulic back-pressure valve) and one of the side openings whereof is connected to a source of the oxidizing agent (not shown). Fitted to a pipe 9 is an electric heater 10 with a controller II of the temperature sensed by a temperature transducer 12 and a flow governor 13 controlling the flow rate of the oxidizing agent.

The electric heater 2 is connected into the load circuit of a controllable voltage source 14, connected in the version described into a variable-ratio autotransformed circuit, the output whereof is applied to the input of a temperature controller 15 having its input connected to a temperature transducer 16 provided in the oven I. The input of the controllable voltage source 14 is connected to a power network by way of a power meter 17.

Depicted in FIG. 2 is a variant of the apparatus for determining the content of combustibles in a gaseous sample of the end products of fuel combustion. Unlike the foregoing version, it dispenses with the sealing arrangement 8. The pipe 9 of this version is integrated with the pipe 6 and is connected directly to the diverging nozzle 5. The pipe 3 is replaced by a pipe 18 which is also connected to the nozzle 5 and is used to introduce the gaseous sample into the oven I by way of ports 19 in the nozzle 5 arranged so as to ensure an intermixing of the sample with the oxidizing agent.

The pipe 18 is provided with an electric heater 20 and a flow governor 21 controlling the flow rate of the sample. The electric heater 20 is provided with a controller 22 of the temperature sensed by a temperature transducer 23.

To maintain the same temperature all the way along the oven I and thus eliminate the error arising from variations in the temperature from point to point in the heating zone, it is preferred to control the temperature in individual areas of the heating zone.

A version of the apparatus wherein the control of temperature is effected in individual areas of the heating zone is represented in FIG. 3. It differs from the apparatus illustrated in FIG. I in that the oven I is provided with an additional electric heater 24 located in the flow of the end products of combustion downstream of the main electric heater 2. Said additional electric heater 24 is connected into the load circuit of a controllable voltage source 25 the output whereof is connected to the output of a temperature controller 26 having its input connected to a temperature transducer 27. Another electric heater 28 is provided in the flow of the end products of combustion downstream of the electric heater 24 and is connected into the load circuit of a controllable voltage source 29 the output whereof is connected to the output of the temperature controller 30 having its input connected to a temperature transducer 31.

The main controllable voltage source 14 is connected with its input to the inputs of the additional sources 25 and 29, the meter 17 being connected into the common external circuit of the voltage sources 14, 25, 29 to measure the aggregate electric power consumed by the electric heaters 2, 24, 28. In the version referred to, the voltage sources 14, 25, 29 are connected in series.

The apparatus materializing the method of determining the content of combustibles in the end products of fuel combustion functions in the following way. A sample of the end products of fuel combustion is introduced from the sampler 4 (FIG. I) over the pipe 3 in a counter-current flow with the oxidizing agent entering the oven I through the diverging nozzle 5. Striking against the walls of the nozzle 5, the particles of the sample disintegrate and are induced to "gush". Thus, they mix well with the oxidizing agent and create favourable conditions for the ignition and burning of the combustibles contained therein.

Before entering the oven I, the oxidizing agent is preheated with the electric heater 10 which is controlled by the temperature controller II operating in conjunction with the temperature transducer 12. Said preheating of the oxidizing agent facilitates the ignition of the combustibles in the sample, shortening, consequently, the period of determining the combustibles content.

After the sample has burned down in the flow of the oxidizing agent, the end product of combustion are expelled from the oven I, for example, into the flue of a boiler plant through the pipe 7.

The temperature in the heating zone of the oven I is measured with the temperature transducer 16 and, in the apparatus shown in FIG. 3, also with the additional temperature transducers 27 and 31. To maintain the temperature in each individual area of the heating zone at a specified constant level, use is made of the temperature controller 15 (FIGS. 1-3) and the additional temperature controllers 26, 30 (FIG. 3) which, being connected each to the respective controllable voltage source 14 (FIGS. 1-3) and the additional voltage sources 25, 29 (FIG. 3), change the voltage across the respective electrical heaters 2 (FIGS. 1-3), 24 and 28 (FIG. 3).

The electric power consumed in maintaining the temperature at the specified constant level varies directly with the amount of heat liberated due to the combustion of the combustibles in the sample. This simplifies the technique of determining the content of combustibles in the end products of fuel combustion, for the amount of the combustibles the sample contains is defined by the calorific value of their burning down. Also simplified is the transformation of the quantity determined into an electric signal.

The sample of the end products of combustion is fed into the oven I (FIGS. 1-3) in metered amounts, using a known feeder, and the flow rate of the oxidizing agent is adjusted so as to be constant with the aid of the flow governor 13.

The heat balance in the heating zone during the combustion of the sample is given by the expression:

$$Q_{p.f.} + Q_c + Q_e = Q_{e.p.} + Q_s + Q_a \quad (1)$$

where $Q_{p.f.}$ is the heat of the products fed into the oven; $Q_c$ is the heat liberated due to the reaction of combustion of the combustibles in the sample; $Q_{e.p.}$ is the heat of the end products; $Q_s$ is the heat lost into the surroundings; $Q_a$ is the heat accumulated in the material of the oven.

The fact that the temperature is maintained at a constant level and so is the rate of feed of the products entering the oven, ensures that the heat balance element $Q_{p.f.}$ remains constant, provided the measurements are taken continuously. Taking into account that the temperature in the heating zone is constant, one can eliminate the quantity $Q_a$ from the heat balance and assume that $Q_{e.p.}$ and $Q_s$ are constant.

The fact that the heat supplied $Q_{p.f.}$ and the heat wasted $Q_{e.p.} + Q_s$ are constant adds to the accuracy of the measurements. These elements of the heat balance can be taken account of by applying a correction A which is constant for a given type of operation of the apparatus and is determined experimentally, using the expression $$A = -(Q_{e.p.} + Q_s) + Q_{p.f.} \quad (2)$$

Hence, the heat balance takes a simplified form $$Q_c + A = Q_e = W \quad (3)$$

where W is the power consumed by the electric heater or heaters and registered by the meter.

The amount, m, of combustibles contained, for example, in the solid end products of combustion is determined from the expression.

$$m = \frac{Q_c}{Q_{c.v.}} = \frac{W - A}{Q_{c.f.}} \quad (4)$$

where $Q_{c.v.}$ is the calorific value of the combustibles contained in the sample of solid end products (a quantity which is practically constant for various grades of the solid fuel tested).

The content, K, of the combustibles in the sample is determined by the formula:

$$K = \frac{m}{m_s} 100, \% \quad (5)$$

where $m_s$ is the mass of the sample for a single determination of the content or the mass flow rate in the case of a continuous determination.

The fact that the elements of the heat balance are maintained constant ensures accuracy in determining the content of combustibles, and the fact that the heat liberated due to the combustion of the combustibles contained in the sample is used to compensate for the power consumed by the electric heater cuts the power requirements.

The possibility of maintaining the constant temperature in the heating zone at a point below that of slagging excludes the slagging and overheating of the heaters, being thus conductive to good realibity of the apparatus.

What is claimed is:

1. A method of determining the content of combustibles in the end products of fuel combustion comprising the steps of:
    taking a sample of end products of fuel combustion;
    introducing said sample into a heating zone of an electric heater;
    introducing an oxidizing agent into said heating zone;
    heating said sample in the heating zone of said electric heater in the presence of said oxidizer to a temperature equal to or higher than the fire point of the combustibles present in said sample, ensuring the burning of said combustibles;
    determining the temperature in the heating zone;
    controlling said electric heater to maintain in said zone a constant temperature during the process of combustion of said combustibles in response to said determined temperature and said constant temperature;
    measuring the power consumed by said electric heater in maintaining said constant temperature in said heating zone; and
    determining the content of said combustibles in response to said measured power.

2. An apparatus for determining the content of combustibles in the end products of fuel combustion, comprising:
    an oven;
    an electric heater located in said oven;
    a first pipe of said oven serving to introduce a sample of the end products of fuel combustion;
    a sampler connected to said first pipe;
    a second pipe of said oven serving to introduce an oxidizing agent;
    a source of said oxidizing agent connected to said second pipe;

a third pipe of said oven serving to discharge the end products of combustion of the combustibles present in said sample;

a temperature transducer located in said oven;

a controllable voltage source having an output, a load circuit and an external circuit, said electric heater being connected into said load circuit;

a temperature controller having an input connected to said temperature transducer and having an output linked with said output of said controllable voltage source; and an electric power meter connected into said common external circuit of said controllable voltage source wherein said power meter measures the power consumed by the electric heater in maintaining said constant temperature in the heating zone whereby the content of said combustibles is determined by said power consumption.

3. An apparatus for determining the content of combustibles in the end products of fuel combustion, comprising:

an oven;

a first pipe of said oven serving to introduce a sample of the end products of fuel combustion;

a sampler connected to said first pipe;

a second pipe of said oven serving to introduce an oxidizing agent;

a source of said oxidizing agent connected to said second pipe;

a third pipe of said oven serving to discharge the end products of combustion of the combustibles present in the said sample;

at least two electric heaters successively located in said oven in the direction of the flow of the end products of combustion through said oven;

a group of temperature transducers, equalling in number with said electric heaters, located in said oven each in the heating zone of said respective electric heater;

a group of controllable voltage sources equalling in number with said electric heaters and having each an input, an output and a load circuit which are electrically interconnected by said inputs and have each said respective electric heater connected into its said load circuit;

a group of temperature controllers, equalling in number with said electric heaters, each having an input connected to said respective temperature transducer and each having an output linked with said output of said respective controllable voltage source;

a common external circuit of said controllable voltage source; and an electric power meter connected into said common external circuit of said controllable voltage sources wherein said power meter measures the power consumed by the electric heaters in maintaining said contant temperature in the heating zone whereby the content of said combustibles is determined by said power consumption.

4. A method of determining the content of combustibles in the end products of fuel combustion comprising the steps of:

taking a sample of end products of fuel combustion;

introducing said sample into a heating zone of an electric heater;

introduction an oxidizing agent into said heating zone;

heating said sample in said heating zone of said electric heater in the presence of said oxidizer to a temperature equal to or higher than the fire point of the combustibles present in said sample, ensuring the burning of said combustibles;

maintaining in said zone a constant temperature during the process of combustion of said combustibles including the steps of selecting a constant value of said temperature to be maintained in the heating zone of the sample with the oxidizing agent, measuring the temperature in the heating zone relative to said constant value as selected, producing a differential signal proportional to the temperature deviation of said measured temperature in the heating zone from the selected constant value thereof, and varying the power of the electric current applied to the electric heater to maintain a constant temperature in the heating zone;

measuring the power consumed by said electric heater in maintaining said constant temperature in said heating zone; and determining the content of said combustibles in response to said measured power.

* * * * *